United States Patent [19]

Winters

[11] Patent Number: 5,059,216
[45] Date of Patent: Oct. 22, 1991

[54] KNEE JOINT REPLACEMENT APPARATUS

[76] Inventor: Thomas F. Winters, 2031 Venetian Way, Winter Park, Fla. 32789

[21] Appl. No.: 414,804

[22] Filed: Sep. 29, 1989

[51] Int. Cl.⁵ .............................................. A61F 2/38
[52] U.S. Cl. .......................................... 623/20; 623/18
[58] Field of Search .................................... 623/20, 18

[56] References Cited

U.S. PATENT DOCUMENTS

| 3,798,679 | 3/1974 | Ewald | 623/20 |
| 4,919,667 | 4/1990 | Richmond | 623/18 |
| 4,963,152 | 10/1990 | Hofmann et al. | 623/18 |

FOREIGN PATENT DOCUMENTS

| 0135319 | 3/1985 | European Pat. Off. | 623/20 |
| 0294298 | 12/1988 | European Pat. Off. | 623/20 |
| 0353921 | 2/1990 | European Pat. Off. | 623/20 |
| 2184025 | 6/1987 | United Kingdom | 623/20 |
| 86/03117 | 6/1986 | World Int. Prop. O. | 623/20 |
| 87/02882 | 5/1987 | World Int. Prop. O. | 623/20 |

Primary Examiner—Randall L. Green
Assistant Examiner—David H. Willse
Attorney, Agent, or Firm—Duckworth, Allen, Dyer & Doppelt

[57] ABSTRACT

During the course of a total knee replacement, at least one and preferably a number of different low friction members having rotated artificial surfaces of different rotated angles are provided in order to determine the appropriate angle and displacement of the aritificial prominence and plateaus on the low friction members, so that the appropriate low friction member may thereafter be permanently installed during the total knee replacement in order to recreate the optimal position.

9 Claims, 2 Drawing Sheets

KNEE JOINT REPLACEMENT APPARATUS

BACKGROUND OF THE INVENTION

The present invention relates generally to apparatus and related methods for repairing or replacing deteriorated joints, and is especially adapted for use in repairing or replacing the human knee joint.

The joint of the human knee is formed by the low friction and movable contact between the femur (thigh bone) and the tibia (shin bone). The upper extremity of the tibia has a surface defined by a generally centrally located prominence, referred to as the intercondular eminence, extending generally longitudinal in the direction of joint motion, the eminence fitting within a corresponding groove in the distal femur. The tibial bearing surface includes a pair of tibial plateaus on opposite sides of the longitudinal eminence which are adapted to act as bearing surfaces for the two ball-shaped bearing surfaces on opposite sides of the femoral groove, called the "femoral condyles". The articulations of the femur and tibia are held together in a movable relationship by the knee cap (patella), and ligaments and muscles extending both inside and outside of the knee, with soft fluidic, cushioning tissue extending between the bearing surfaces.

Frequently, a deteriorated knee requires the replacement of the bearing surfaces of the upper portion of the tibia and the lower portion of the femur; this is customarily referred to as a "total knee replacement". Because a total knee replacement involves the cutting away of a substantial portion of the upper portion of the tibia and the lower portion of the femur and with replacement of those two portions with artificial components, then these artificial components must employ low friction surfaces which are capable of cooperating together to simulate as closely as possible the natural movement of the human knee before surgery.

A total knee replacement usually involves the removal of approximately between 0.5 to 1.5 centimeters of the upper portion of the tibia, including both the longitudinal eminence and the tibial plateaus, leaving a relatively flat surface into which a rigid metal support member is inserted. Then, a low friction bearing member is affixed to the support member, with the low friction member including a longitudinal prominence simulating the eminence and with bearing surfaces simulating the tibial plateaus. A lower end portion of the femur is then removed, and a member having bearing surfaces replicating the femoral condyles is then affixed to the remaining end of the femur.

SUMMARY OF THE INVENTION

The present invention is based upon the discovery and observations that the rotation of the naturally occurring tibial plateau may not be replicated in the bearing surface of the artificial low friction member, which may hinder the natural movement of the knee. Accordingly, there has been devised a method for providing a number of low friction insert members having different rotational relationships, so that during the course of a total knee replacement, different low friction members having rotated artificial surfaces of different rotated angles may be installed upon the support member. The knee is then moved through a range of motion to determine the appropriate angle and displacement of the artificial prominence and plateaus, and thereafter permanently installing a member having the appropriate rotational disposition, thereby recreating the optimal position.

Accordingly, the present invention also contemplates a prosthesis for replacing the proximal aspect of the tibia, with the prosthesis comprising a member with a low friction surface having a longitudinal prominence designed to simulate and replace the natural eminence extremity of the tibia. It will of course be understood that the longitudinal prominence of the bearing member surface is centrally disposed, with two recessed portions on either side of the prominence adapted to receive a femoral bearing surface, with the two recesses being rotated substantially as the longitudinal prominence of the prosthesis and displaced in an anterior or posterior direction to optimize correct knee motion.

Generally, the angle of rotation of the longitudinal prominence of the prosthesis is leftwardly for a left knee and rightwardly for a right knee, with the angle of rotation being on the order of between 3° –15°, although other rotational displacements may be appropriate in certain cases. It will be understood from the above discussion regarding the method of the present invention that a number of prostheses with different specific rotational displacements will be provided, so that the appropriate rotational displacement can be selected during the course of the surgery.

THE DRAWING

DETAILED DESCRIPTION OF THE DRAWING

A preferred embodiment of the present invention will now be described with reference to the drawings.

Figure 1:
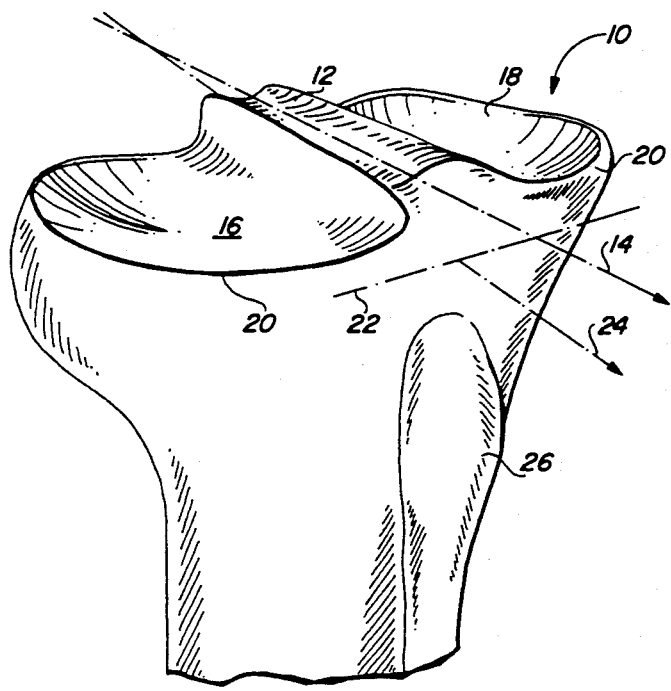
FIG. 1 is a perspective view of the top portion of the human tibia before a total knee replacement operation.

FIG. 1 illustrates the upper extremity of a human tibia 10, which includes a tibial eminence 12. The shape and dimensions of the eminence 12 vary, of course, from individual to individual. Nevertheless, the eminence generally extends in a longitudinal direction defined by dotted line 14 between the front and rear of the tibia. A pair of tibial plateaus 16, 18 are positioned on opposing sides of the eminence 12, and are adapted to receive the ball-shaped bearing surfaces at the lower extremity of the femur (see, for example, the artificial bearing surfaces 74 and 76 attached to the femur 70 in FIG. 12). The tibial plateaus 16, 20 are defined by an outer peripheral edge 20.

Dotted line 22 in FIG. 1 lies in a plane approximately where a cut is typically made during a total knee operation, in order to remove the upper portion of the tibia 10. Of course, when the upper portion is removed, the eminence 12, ridge 20 and plateaus 16, 18 are removed as well. The resulting cut across the plane defined by line 22 generally lies on the order of between 0.5 and 1.5 centimeters below the top of the tibia, in the direction of the tibia tubarcle 26. The cut is usually flat across the tibia 10. It has been discovered that the longitudinal direction across the cut at about line 22 results in a significant displacement in the longitudinal direction between the front and rear of the tibia across the cut, as is illustrated by the dotted line 24. This angular displacement is caused by the change in the rotational disposition of the tibia downwardly toward the tibial tubarcle 26 from the upper extremity of the tibia 10.

Figure 3:
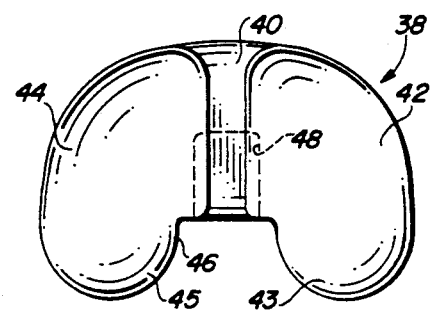
FIGS. 3, 4 and 5 are top plan, front and side views, respectively, of a prior art bearing surface prosthesis like that illustrated in FIG. 2.
Figure 4:
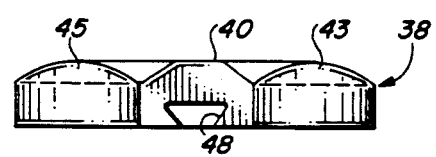
Figure 2:
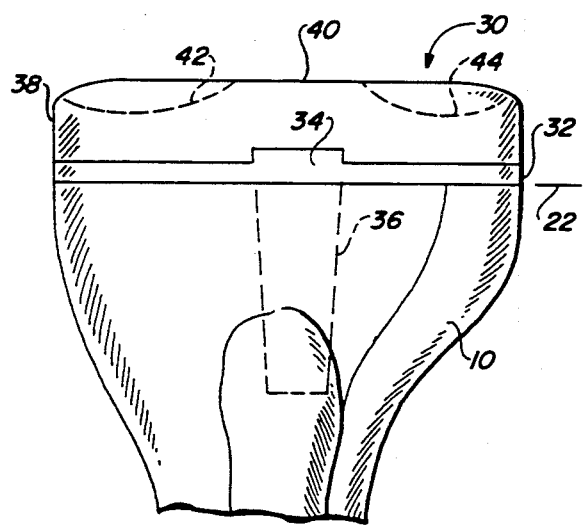
FIG. 2 is a front elevation of a human tibia after implantation of a prior art total knee prosthesis.
Figure 5:
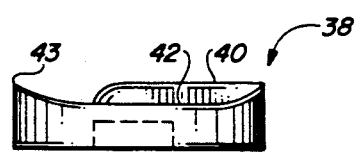

In the prior art, as shown in FIGS. 2-5, it has been customary to affix a support member 32 to the cut surface as defined by line 22, with the support member 32 having a peg 36 ektending into the tibia 10 to fit the prosthesis to the bone. The surface 34 of the member 32 is dimensioned to receve a low friction member 38. The prior art arrangements for' the low friction member 38 include a longitudinal prominence 40 which extends longitudinally front to rear (see FIG. 3), and a pair of recessed areas 42, 44 which simulate the tibial plateaus 16, 18 and are adapted to provide a low friction surface for the artificial femur bearing surfaces 74, 76 attached to the femur 70 as part of a total knee replacement (FIG. 12), As shown in FIGS. 3-5, the prior art bearing member may include a rear indentation and ridges 43, 45 which surround the respective plateaus 42, 44.

Figure 6:
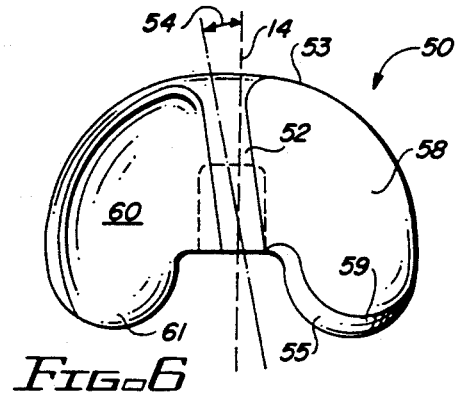
FIGS. 6, 7 and 8 are top plan, front and side views, respectively, of a tibial bearing surface insert for a left knee in accordance with the present invention.
Figure 8:
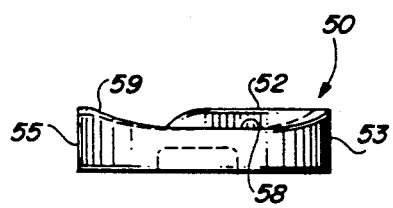
Figure 7:
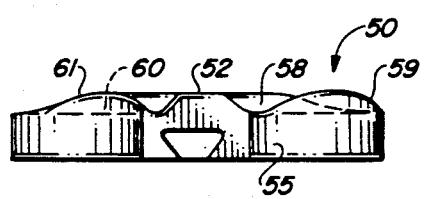
Figure 9:
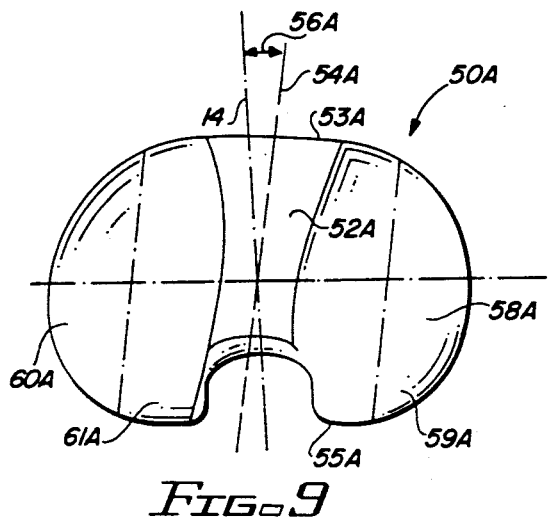
FIGS. 9, 10 and 11 are top plan, rear and side elevations, respectively, of an insert for a right knee in accordance with the present invention.
Figure 10:
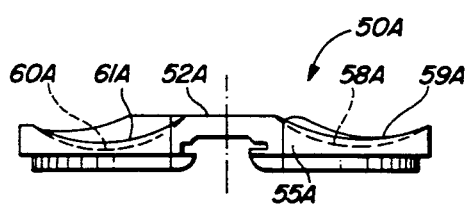
Figure 11:
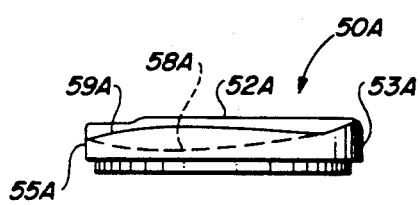

Low friction bearing members 50, 50A in accordance with the present invention will now be described with reference to FIGS. 6-8 and 9-11, respectively. The arrangement shown in FIGS. 6-8 is designed for use with a left knee, and the arrangement of FIGS. 9-11 is designed for use with a right knee. In FIGS. 6-8 and 9-11, common reference numerals are utilized for the same drawing elements.

The perspective bearing member 50, 50A includes a front surface 53, 53A and a rear surface 55, 55A. An offset longitudinal prominence 52, 52A extends angularly between the front and rear of the bearing member 50, 50A at a respective angular displacement which may be determined during the course of a total knee operation, as described in greater detail below (or which may determine pre-operatively through the use of CT scanning techniques). That angular displacement is shown by the angular arrow 56, 56A between the longitudinal line 14 and another dotted line 54, 54A. Each of the bearing members 50, 50A includes a first recess portion 58, 58A and a second recessed portion 60, 60A designed to simulate the tibial plateaus 16, 18 of the tibia 10 (FIG. 1). Each recessed portion 58, 58A, 60, 60A has a respective ridge 59, 59A, 61, 61A surrounding the recess. As noted above, the angular displacement reflected by angle 56, 56A is typically on the order of between about 3°-15°, although other angles may be utilized in certain cases. It is contemplated that a number of bearing members for a left knee and a number of bearing members for the right knee having different angular configurations would be provided in advance of a total knee operation, so that the surgeon may select the appropriate angular displacement during the course of the operation. Alternatively, CT scans prior to the operation may be utilized to define the optimal angle of rotation for the prosthesis member 50, 50A.

Figure 12:
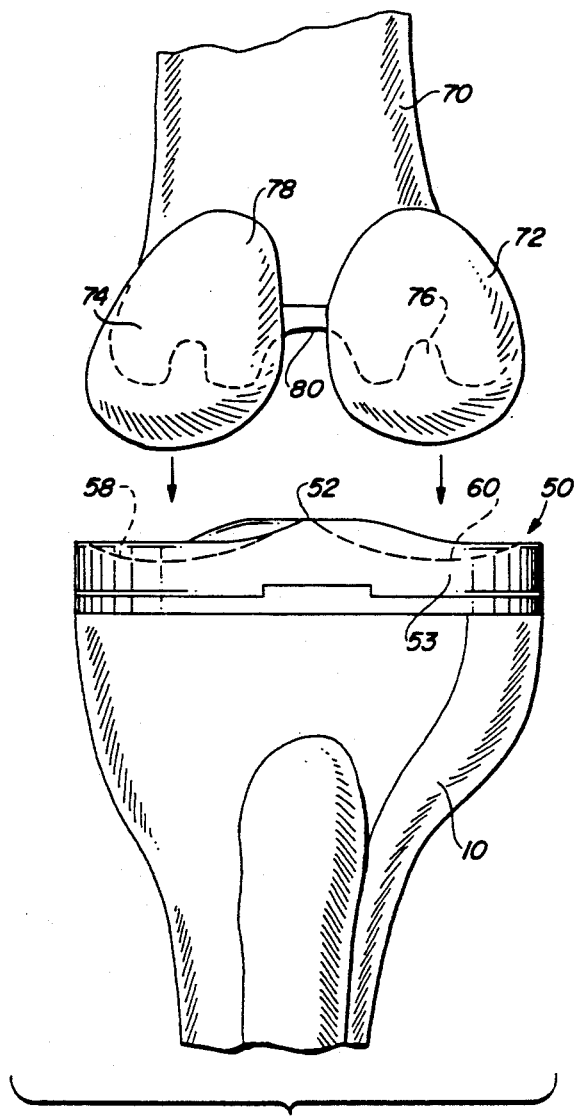
FIG. 12 is a front view of the tibia and femur after a total knee replacement using the method of the present invention.

A total knee surgical procedure of course exposes the upper end of the tibia 10. Thereafter, a lateral cut is placed across the top of the tibia 10, generally in the plane of line 22 (FIG. 1), to remove a small portion of the upper end of the tibia 10 at the knee. The removed portion includes the natural eminence 12 and the bearing surfaces 16, 18 for the femoral bearing surfaces. Thereafter, the support member 32 is be fixed to the cut surface. A prosthesis, such as bearing member 50 in FIG. 12, is temporarily installed upon the support member 32. The longitudinal prominence 52 of the bearing member 50 is rotated at a substantial angle with respect to the longitudinal direction of the tibia 10 across the cut surface 22 as is described above. After insertion of a first bearing member having a particular angular displacement for the longitudinal prominence 52, it is then moved to determine knee motion for correctness of the rotation of the angle. If the angle is inappropriate, another bearing member 50 is selected and the process continued until the proper angular displacement is achieved. Thereafter, the bearing member 50 is permanently installed. As is shown in FIG. 12, it would also be customary to remove a portion of the femur 70 including a portion of its natural bearing surfaces, and the installation of an artificial femoral bearing surface 72, 74 which is separated by a groove 80 dimensioned to mate with and receive the rotated longitudinal prominence 52.

In a significant number of cases, the rotated longitudinal prominence of the present invention will result in a substantial improvement in the function of the joint after a total knee operation.

What is claimed is:

1. A prosthesis for replacing the knee extremity of a human tibia, the prosthesis comprising a member with an upper low friction and a low surface, the upper surface having a longitudinal prominence for replacing the natural eminence of the tibia across the knee extremity, the longitudinal prominence of the prosthesis rotated by a substantial angle with respect to the direction along a line from the posterior of the lower surface to the interior of the lower surface.

2. The prosthesis recited in claim 1, further comprising means for joining the member to the tibia after removal of the knee extremity of the tibia.

3. The prosthesis recited in claim 1 wherein the longitudinal prominence of the upper surface is centrally disposed, the surface further comprising two recessed portions, one portion on either side of the longitudinal prominence of the surface, each recessed portion adapted to receive a femoral bearing and being rotated substantially as the longitudinal prominence of the surface.

4. The prosthesis recited in claim 1 wherein the angle of rotation is leftwardly for a left knee prosthesis and rightwardly for a right knee prosthesis.

5. The prosthesis recited in claim 1 wherein the angle of rotation is on the order of between about 3°-15°.

6. A method for replacing the upper extremity of a human tibia, comprising the steps of:
   conducting a surgical procedure to expose the upper end of the tibia;
   cutting laterally across the top of the tibia to remove a small portion of the upper end of the tibia at the knee, including the natural eminence and the bearing surface for the femoral bearing surfaces;
   fixing a support member across the surface of the cut end of the tibia;
   providing a plurality of bearing members, each bearing member having a low friction surface with a prominence simulating the natural tibial eminence, the prominence of each bearing member positioned at a substantial angle with respect to the longitudinal direction of the tibia across the cut surface from the rear of the knee to the front of the knee;

temporarily installing one of the bearing members on the support surface;

moving the tibia through a knee motion while the one bearing member is temporarily installed to determine the correctness of the angle of the prominence; and thereafter permanently installing one of the bearing members having the desired angle of rotation.

7. The method recited in claim 6 further comprising the step of removing a portion of the femur opposite the upper end of the tibia, and affixing a prosthesis to the femur which appropriately mates with the rotated member installed upon the tibia.

8. The method recited in claim 6 wherein the cutting step comprises removing on the order of about 0.5 to 1.5 centimeters of the upper end of the tibia.

9. A method for repairing a human knee joint by replacing portions of the femur and tibia at the knee comprising the steps of:

cutting an end portion of the tibia including the natural eminence and the tibial bearing surface which normally contacts with the lower portion of the femur, and exposing a cut surface of the tibia;

installing an artificial member upon the exposed cut surface of the tibia, the artificial member having a low friction surface with an artificial eminence and artificial bearing surfaces, the artificial eminence rotated at a substantial angle with respect to the longitudinal direction of the tibia across the exposed cut surface from the rear of the knee to the front of the knee;

removing an end portion of the femur including the natural bearing surfaces; and installing a member having an artificial femoral bearing surface separated by a groove dimensioned to mate with and receive the rotated longitudinal artificial eminence.

* * * * *

UNITED STATES PATENT AND TRADEMARK OFFICE
CERTIFICATE OF CORRECTION

PATENT NO. : 5,059,216
DATED : October 22, 1991
INVENTOR(S) : Thomas F. Winters

It is certified that error appears in the above-indentified patent and that said Letters Patent is hereby corrected as shown below:

Col. 4, Line 31: After "friction" insert --surface--;

Col. 4, Line 31: Delete "low" (second instance), and insert --lower-- therefor;

Col. 4, Lines 36-37: Delete "interior" and insert --anterior-- therefor;

Col. 4, line 43: After "the" insert --upper--.

Signed and Sealed this

Thirteenth Day of May, 1997

Attest:

BRUCE LEHMAN

Attesting Officer

Commissioner of Patents and Trademarks